United States Patent [19]

Simonovitch

[11] 4,195,087

[45] Mar. 25, 1980

[54] DERIVATIVES OF NAPHTHYRIDINE

[75] Inventor: Chaim Simonovitch, Rishon le Zion, Israel

[73] Assignee: Abic, Ltd., Ramat Gan, Israel

[21] Appl. No.: 857,900

[22] Filed: Dec. 6, 1977

[30] Foreign Application Priority Data

Dec. 10, 1976 [IL] Israel .................................... 51092

[51] Int. Cl.$^2$ ............................................ C07D 471/04
[52] U.S. Cl. ...................................... 424/256; 542/406; 542/416; 542/417; 542/418; 542/419; 542/420; 546/123
[58] Field of Search ................................ 542/416–420, 542/406; 260/295 N, 295.5 B; 424/256

[56] References Cited

U.S. PATENT DOCUMENTS

| | | | |
|---|---|---|---|
| 3,149,104 | 9/1964 | Lesher | 260/295 N |
| 3,516,994 | 6/1970 | Lesher | 542/407 |
| 3,829,492 | 8/1974 | Miller et al. | 542/418 |
| 3,846,413 | 11/1974 | Seng et al. | 542/418 |
| 3,997,528 | 12/1976 | Yoshioka et al. | 542/419 |
| 4,011,214 | 3/1977 | Terao et al. | 542/416 |

Primary Examiner—Arthur P. Demers
Attorney, Agent, or Firm—Steinberg & Blake

[57] ABSTRACT

The present invention deals with derivatives of naphthyridine, process for their preparation and their utility, inter alia, as anti-bacterides and as feed-additives.

26 Claims, No Drawings

DERIVATIVES OF NAPHTHYRIDINE

The present invention consists in 3-carboxy-4-oxo-1,4-dihydro-1,8-naphthyridines of general formula I

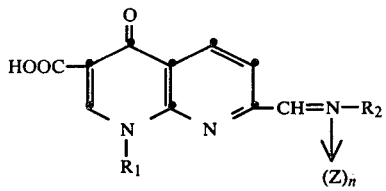

in which $R_1$ stands for a straight or branched alkyl radical having 1-7 carbon atoms or for a cycloalkyl radical, Z stands for oxygen, n stands for 0 or 1 and $R_2$ is selected among the group comprising the following OH; $C_6H_5$; —$NHR_1$,

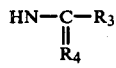

($R_3$ standing for a radical selected among the group comprising a straight or branched alkyl radical having 1-7 carbon atoms; or for a cycloalkyl radical; $NH_2$; $NHNH_2$; $OR_1$; and a phenyl radical optionally substituted by a OH or $NO_2$ group and $R_4$ standing for O or NH); $C_6H_5$—$R_1$; $C_6H_5$—Hal (Hal standing for a halogen atom); and a heterocyclic radical, e.g.

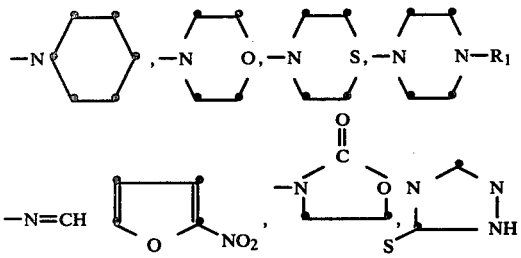

and in the physiologically acceptable salts thereof.

Some compounds of general formula II

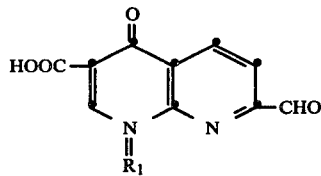

in which $R_1$ has the same meaning as in general formula I are known (U.S. Pat. No. 3,404,153). The pharmaceutical properties of some of the compounds of formula II are known. However, their antibacterial properties are unsatisfactory.

It has now been found that the compounds of general formula I have a better antibacterial activity than the compounds of formula II. Moreover they have a surprising activity against fungi, and against protozoa.

Some compounds of general formula I have a significant in vivo activity against gram negative bacteria, e.g. *E. coli* and *Proteus mirabilis* 333 in mice and in urinary tract infections caused by *E. coli* in mice when administered at a dose of 100 mg/kg per day for short periods of time. Moreover, some of said compounds had low sub-cutaneous acute toxicity ($LD_{50}$ in the order of 800 mg/kg) in comparison with that of nalidixic acid the $LD_{50}$ of which is about 500 mg/kg.

The new compounds of general formula I may be administered per se, but are usually administered as the active part of a composition, i.e., in the form of tablets, capsules, ampules, suppositories, suspensions or solutions. Said compositions are prepared in a conventional manner, i.e., by addition of a suitable pharmaceutically acceptable binder, extender, carrier, emulsifier, solvent, other suitable therapeutic compounds and the like.

Moreover, the new compounds of general formula I may also be utilised as feed additives, or may be part of a feed pre-mix.

Moreover, the salts of the compounds of general formula I may be dissolved in water and thus applied to warm and cold blooded animals in drinking water.

The present invention consists also in a process for the preparation of compounds of general formula I in which a compound of general formula II is reacted with a compound of general formula III $$KH_2—R_2$$

in which $R_2$ has the same meaning as above. The reaction is performed in an inert solvent, preferably in an alcohol, e.g., ethanol or an ethanol/water mixture, and, if desired, in the presence of an acid. The temperature range is preferably about 20° to the boiling temperature of the solvent and/or the amine.

The present invention will now be illustrated with reference to the following Examples without being limited by them. All temperatures are indicated in degrees Centigrade. All melting points are uncorrected.

EXAMPLE 1

Into a 100 ml 3-necked flask equipped with an efficient mechanical stirrer reflux condenser and a dropping funnel were introduced 7.95 g of 1-amino-4-methyl-piperazine in 100 ml of absolute ethanol. 15.3 ml of concentrated hydrochloric acid were introduced causing the precipitation of the hydrochloric salt. Stirring was continued for fifteen minutes at room temperature.

In another three-necked flask equipped with an efficient mechanical stirrer were suspended 15.6 g of 1-ethyl-7-formyl-3-carboxy-4-oxo-1,4-dihydro-1,8-naphthyridine in 100 ml absolute ethanol. The amino piperazine salt suspension was added in one portion, and the mixture was heated to reflux with stirring.

A short time after the heating commenced, most of the materials went into solution and after that the product began to precipitate out.

Reflux was continued for three hours. The solution filtered while hot to yield 9.4 g of (1-(-7(1-ethyl)-3-Carboxy-4-oxo-1,4-dihydro-1,8-naphthyrilidene amino))-4-methyl piperazine HCl m.p. 288° C. The product was washed several times with hot ethanol (95%) without changing the melting point.

When tested in vitro according to standard bacteriological evaluation it was found that the compound had a broad anti-bacterial activity, as is shown for example, in Table I.

TABLE I

| Micro-organism | Minimal Inhibitory concentration in μg/ml |
|---|---|
| *Staph. aur.* | 5 |

TABLE I-continued

| Micro-organism | Minimal Inhibitory concentration in μg/ml |
| --- | --- |
| Shig. boydii | 12 |
| Shig. flex | 6 |
| Salm. typh. | 10 |
| E. Coli | 0.5–2 |
| Klebsiella | 12 |
| Proteus mireb. 3333 | 25 |
| Pseud. aur. | 100 |
| Herrela | 25 |

It was found that the compound was significant in vivo activity against systemic infection in mice caused by E. coli when administered per os at a dose level as low as 100 mg/kg per day.

The compound also showed protection against experimental pyelonephritis in mice caused by E. coli at a dosage of 100 mg/kg per day for three days. Acute subcutaneous toxicity ($LD_{50}$) in mice was found to be of the order of 800 mg/kg.

The compound showed activity against resistant strains of E. coli as indicated in Table II.

TABLE II

| xx095 | 091xx | xx096 | 8090x | 8097x | E.Coli Strain |
| --- | --- | --- | --- | --- | --- |
| 1.2 | 5 | 2 |  | 25 | Example 1 |
|  |  |  | 200 | 500 | Nalidixic acid | x Nalidixic acid Resistant
xx Streptomycin resistant

EXAMPLE 2

In the same manner as described in Example 1, there were prepared:
a. 1-[7(1-ethyl-3 carboxy-4-oxo-1,4 dihydro-1,8 naphthyrilidene amino)]pyrolidine; m.p. 285°.
b. 1-[7(1-ethyl-3 carboxy-4-oxo-1,4 dihydro-1,8 naphthyrilidene amino)]morpholine; m.p. 250°. This compound exhibited antifungal activity in vivo against C.albicans at a concentration of 25 μg/ml.
c. 1-[7-(1-ethyl-3 carboxy-4-oxo-1,4 dihydro-1,8 naphthyrilidene amino)]piperidine; m.p. 250°.

EXAMPLE 3

A mixture containing 2 g of 7-formyl-3-carboxy-4-oxo-1, 4-dihydro-1,8-naphthyridine and 0.51 g of acethydrazide and 20 ml of ethanol are stirred and refluxed for 1½ hours. The mixture was cooled and the solids were filtered and washed with a little ethanol and dried at room temperature. Several washings with hot cellosolve and dimethyl formamide yielded 2 g of 1-ethyl-3-carboxy-4-oxo-1, 4 dihydro-1,8 naphthyridine-7 carboxaldehyde acethydrazone m.p. 300°.

When tested in vitro according to standard bacteriological evaluation it was found that the compound possessed broad anti-bacterial activity as shown in Table III.

TABLE III

| Micro-organism | Minimal inhibitory concentration in μg/ml |
| --- | --- |
| Staph. aur. | 6 |
| Shig. boydii | 12 |
| Shig. flex. | 12 |
| Salm. typh. | 50 |
| E. Coli | 6–12 |
| Klebsiella | 25 |
| Prot. mirab. 3333 | 12 |
| Pseud. aur. | 100 |
| Herella | 50 |

The compound showed protection against experimental pyelonephritis in mice caused by E.coli at a dose of 100 mg/kg per day for three days.

EXAMPLE 4

A mixture of 2.5 g of 1-ethyl-7-formyl-3-carboxy-4-oxo-1, 4-dihydro 1,8-naphthyridine and 1.5 g of 4 hydroxy benzoic acid hydrazid dissolved in 50 ml of ethanol were refluxed for 2 hours. The solid went into the solution in the first period of heating and crystallized out later on. The suspension was then cooled, the solids filtered off and dried at room temperature. Several washings with dimethyl formamide yielded 2 g of 1-ethyl-3-carboxy-4-oxo-1,4-dihydro-1,8 naphthyridine-7-carboxaldehyde-(4'hydroxy phenyl)hydrazone; m.p. 300°. The compound was hard to solubilize for in vitro screening, but showed activity against E. coli at a dose of 50 μg/ml.

EXAMPLE 5

In the same manner as described in Example 4 there were prepared:
a. 1-ethyl-3-carboxy-4-oxo-1,4 dihydro-1,8 naphthyridine-7-carboxyaldehyde-(4 nitro phenyl)hydrazone; m.p. 290°.
b. 1-ethyl-3-carboxy-4-oxo-1,4 dihydro-1,8 naphthyridine-7-carboxaldehyde(2 nitro phenyl)hydrazone; m.p. 250°.

EXAMPLE 6

1 g of ethyl carbazate and 2.5 g of 1-ethyl-7-formyl-3-carboxy-4-oxo-1,4-dihydro-1,8 naphthyridine were suspended in 25 ml of methanol. A few drops of concentrated hydrochloric acid were added and the mixture was stirred and refluxed for 3 hours. The mixture was then stirred over-night at room temperature and the solids obtained were filtered off and dried at room temperature. Recrystallization from dimethyl formamide water yielded 1 g of 1-ethyl-3-carboxy-4-oxo-1,4 dihydro-1,8-naphthyridine-7 carboxaldehyde ethyl carbazone; m.p. 270°(dec.).

The compound had an in vitro activity against E.coli and C.albicans and concentration of 25 μg/ml and 50 μg/ml respectively.

EXAMPLE 7

In the same manner as described in Example 6 there were prepared:
a. 1-ethyl-3-carboxy-4-oxo-1,4-dihydro-1,8 naphthyridine-7-carboxaldehyde-thio carbohydrazone; m.p. 240°.
b. 1[7 -(1-ethyl-3-carboxy-4-oxo-1,4 dihydro-1,8-naphthylidene amino)]2 mercapto 1, 3, 5 triazole; m.p. 200°.

EXAMPLE 8

1.5 g of 5-nitrofuryl hydrazone and 2.5 g of 1-ethyl-7-formyl-3-carboxy-4-oxo-1, 4-dihydro-1, 8-naphthyridine were suspended in 20 ml of ethanol and the mixture was refluxed for 1 hour. The solution was cooled and filtered. Crystallization of the product from nitromethane yielded 2 g of N-[7(1-ethyl-3 carboxy-4-oxo-1.4 dihydro-1,8 naphthyrilidene)-N-(2-(nitrofuryliden)]-azine. m.p. 245°.

When tested in vitro according to standard bacteriological evaluation it was found that the compound possessed broad bacterial activity as shown, for example in Table IV.

TABLE IV

| Micro-organism | Minimal inhibitory concentration in μg/ml |
|---|---|
| Staph. aur. | 12.5 |
| Shig. boydii | 12 |
| Shig. flex | 25 |
| E. Coli | 6 |
| Salm. | 25 |
| Klebs | 25 |
| Pseud. aur. | 200 |
| Herella | 25 |
| C. albicans | 25 |

The compound also showed in vitro activity against trichomonas Vaginalis at a concentration of 1 μg/ml.

It was found that the compound had a significant in vivo activity against experimental pyelonephritis caused by E.coli in mice at a dosage of 100 mg/kg/day for three days.

EXAMPLE 9

100 mg of 1-ethyl-7-formyl-3-carboxy-4-oxo-1, 4-dihydro-1, 8-naphthyridine was suspended in 5 ml of methanol. The mixture was stirred and brought to reflux. To this suspension was added 30 mg of hydroxyl amine hydrochloride dissolved in 1 ml of water. The mixture was heated at reflux for 1 hour, cooled and the solids obtained were filtered off and washed with cold dilute ammonia solution. Recrystallization from dimethyl formamide and water yieled 1-ethyl-3-carboxy-4-oxo-1, 4 dihydro-1,8 naphthyridine-7-carboxaldomime; m.p. 270°.

When tested in vitro according to standard bacteriological evaluation it was found that the compound possessed broad antibacterial activity as shown, for example, in Table V:

TABLE V

| Micro-organism | Minimal inhibitory concentration in μg/ml |
|---|---|
| Stap. aur. | 12.5 |
| Shig. boydii | 1.5 |
| Shig. flex | 1.5 |
| Salm. typh. | 12 |
| E. Coli | 1.5 |
| Klebs | 6 |
| Proteus mirabilis 3333 | 3 |
| Pseud. aur. | 200 |
| Herella | 6 |

It was found that the compound had a significant in vivo activity against systemic infection in mice caused by E.coli at a dose of 100 mg/kg per day for three days.

EXAMPLE 10

In the same manner as described in Example 9 the following compounds were prepared:
a. 1-Ethyl-3-carboxy-4-oxo-1;4-dihydro-1,8-naphthydrine-7 carboxaldehyde semicarbazone; m.p. 305°.
b. 1-[7(1-Ethyl-3-carboxy-4-oxo-1;4-dihydro-1,8-naphthyrilidene amino)]guanidine; m.p. 270°.
c. 1-Ethyl-3-carboxy-4-oxo-1;4 dihydro-1,8-naphthyridine-7 carboxaldehyde carbohydrazone; m.p. 285°.
d. 1-[7-(1-ethyl-3-carboxy-4-oxo-1,4-dihydro-1;8-naphthyrilidene amino)]oxazolidone; m.p. 300°.

EXAMPLE 11

167 mg of N-(hydroxyethyl) hydroxyl amine oxalate was dissolved in 5 ml of water, and 167 mg of sodium bicarbonate were added and the mixture was stirred at room temperature for 5 minutes. 271 mg of 1-ethyl-7-formyl-3-carboxy-4-oxo-1, 4-dihydro-1,8-naphthyridine were added in one portion and the mixture was stirred at room temperature for 24 hours. The solids obtained were filtered off and crystallized from dimethyl formamide and water yielded 120 mg of 1-ethyl-3-carboxy-4-oxo-1,4 dihydro-1,8-naphthyridine-7-carboxaldehyde($\beta$-hydroxyethyl)nitrone; m.p. 230°.

The compound inhibited E.coli at a concentration of 12.5 μg/ml.

EXAMPLE 12

In the same manner as described in Example 11 there was prepared starting from ethyl Hydrazine oxalate: 1-ethyl-3-carboxy-4-oxo-1,4 dihydro-1,8-naphthyridine-7-carboxaldehyde (N-ethyl)hydrazone; m.p. 230°.

EXAMPLE 13

250 mg of 1-ethyl-7-formyl-3-carboxy-4-oxo-1,4-dihydro-1, 8-naphthyridine and 200 mg of aniline were added to 10 ml of anhydrous ethanol. A few drops of concentrated hydrochloric acid were then added and the mixture was refluxed for 12 hours. The solids obtained were filtered off and washed with a little ethanol. Crystallization from nitromethane gave 200 mg of 1-ethyl-3-carboxy-4-oxo-1,4-dihydro-1,8-naphthyridine-7-(phenylene-amino)carboxaldehyde; m.p. 290°.

The compound inhibited the growth of E.coli and C.albicans at a concentration of 12.5 μg/ml.

EXAMPLE 14

In the same manner as described in Example 13, there were prepared:
a. 1-ethyl-3-carboxy-4-oxo-1,4-dihydrol-1.8-naphthyridine-7-[(4-ethoxy-phenylamino)]carboxaldehyde; m.p. 270°.
b. 1-ethyl-3-carboxy-4-oxo-1,4-dihydro-1,8-naphthyridine-7-carboxaldehyde phenyl nitrone; m.p. 230°.

The nitrone inhibited the growth of E.coli at a concentration of 12.5 μg/ml.

EXAMPLE 15

250 g of 1-ethyl-3-carboxy-4-oxo-1,4-dihydro-1,8-naphthyridine-7-carboxaldoxime is mixed with 80 g of lactose and 8 g of silicon (Aerosil), the mixture is filled into capsules with an appropriate machine. Each capsule thus weighs 338 mg.

EXAMPLE 16

500 g 1-[7'-(1'-ethyl-3' carboxy-4'oxo-1,4 dihydro-1, 8-naphthyrilidene amino)]-4-methylpiperazine.
100 g Corn starch
15 g Magnesium stearate
10% Starch paste 10% of starch paste is prepared and used for the granulation of the active principle. The granulate is passed through a size 12 stainless steel screen and dried in a Colton oven for 8 hours. The dried granulation is passed through 20 mesh stainless steel screen. Pre-screened (size 60 mesh screen) corn starch and magnesium stearate and the mixture blended in a tween cone blender for 10 minutes, the mixture is removed and compressed into tablets weighting 620 mg using an appropriate punches.

EXAMPLE 17

7 g 1-(7'(1'-ethyl-3'carboxy-4-oxo-1,4 dihydro-naphthyrilidene amino))-4-methyl piperazine.
1 g hydrated aluminium silicate (Vee gum)
0,2 g methyl p-hydroxy benzoate
0,02 g propyl p-hydroxy benzoate
0.15 g Sodium Saccharine
9.5 Flavour and Colour
Add distilled water up to 100 ml.
Recommended dose 1 teaspoon os suspension (5 ml equivalent to 350 mg of the active agent).

EXAMPLE 18

| | |
|---|---|
| 1-[-7(1-ethyl-3-carboxy-4-oxo-1,4 dihydro-1,8-naphthyridene amino)/ ]-4-methyl piperazine; m.p. 285°. | 15.00 g |
| Cane Sugar | 100.00 g |
| Soybean residue (after extraction) 885.00 g | |
| Total weight | 1,000.00 g |

The ingredients are intimately mixed and the resulting mixture serving as feed additive may be added in the desired amount to any desired feed. For example such a feed may comprise:

| Ingredients | g |
|---|---|
| Alfalfa flour | 50 |
| Yellow maize | 1225 |
| Gluten flour | 50 |
| Animal fat | 40 |
| Dried malt brewers grains | 25 |
| Fish meal | 100 |
| Oyster shells | 15 |
| Poultry feed additive | 100 |
| Soybean flour | 380 |
| Salt | 5 |
| Dicalcium | 15 |
| Vitamin mixture | 5 |
| Mixture of trace elements | 0.5 |
| | 2000.50 |

The above feed additive is added to the well mixed ingredients of the feed.

I claim:
1. 3-Carboxy-4-oxo-1,40dihydro-1, 8-napthyridines of the formula

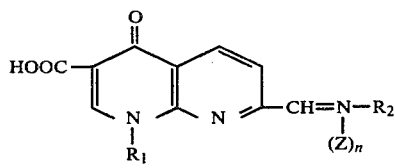

wherein $R_1$ is selected from the group consisting of straight and branched alkyl of 1–7 carbon atoms and cycloalkyl, Z stands for oxygen, n is 0 or 1, and $R_2$ is selected from the group consisting of the group OH; the group $C_6H_5$; the group $-NHR_1$ wherein $R_1$ has the same definition as above; the group

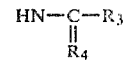

wherein $R_3$ is selected from the group consisting of straight and branched alkyl of 1–7 carbon atoms, cycloalkyl, $NH_2$, $NHNH_2$, $OR_1$ wherein $R_1$ has the same definition as above, phenyl, phenyl—OH and phenyl—$NO_2$ and wherein $R_4$ stands for O or NH; the group $C_6H_5-R_1$ wherein $R_1$ has the same definition as above; the group $C_6H_5$—Hal wherein Hal is a halogen; and a heterocyclic group selected from the group consisting of

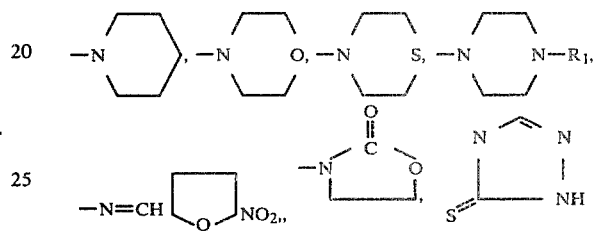

wherein $R_1$ has the same definition as above; and physiologically acceptable salts thereof.

2. Compound according to claim 1 being 1-[-7(1-ethyl-3-carboxy-4-oxo-1,4-dihydro-1,8-naphthyrilidene amino)]-4-methyl piperazine HCl.

3. Compound according to claim 1 being 1-[7(1-ethyl-3-carboxy-4-oxo-1,4-dihydro-1,8-naphthyrilidene amino)]pyrolidine.

4. Compound according to claim 1 being 1-[7(1-ethyl-3-carboxy-4-oxo-1,4 dihydro-1,8-naphthyrilidene amino)]morpholine.

5. Compound according to claim 1 being 1-[7-(1-ethyl-3-carboxy-4-oxo-1,4-dihydro-1,8-naphthyrilidine amino)]piperidine.

6. Compound according to claim 1 being 1-ethyl-3-carboxy-4-oxo-1,4-dihydro-1,8-naphthyridine-7 carboxaldehyde acethydrazone.

7. Compound according to claim 1 being 1-ethyl-3-carboxy-4-oxo-1, 4-dihydro-1,8-naphthyridine-7-carboxaldehyde-(4'hydroxyphenyl)hydrazone.

8. Compound according to claim 1 being 1-ethyl-3-carboxy-4-oxo-1, 4-dihydro-1,8-naphthyridine-7-carboxaldehyde-(4 nitro-phenyl) hydrazone.

9. Compound according to claim 1 being 1-ethyl-3-carboxy-4-oxo-1, 4-dihydro-1,8-naphthyridine-7-carboxaldehyde(2-nitro-phenyl) hydrazone.

10. Compound according to claim 1 being 1-ethyl-3-carboxy-4-oxo-1, 4 dihydro-1,8-naphthyridine-7-carboxaldehyde ethyl carbazone.

11. Compound according to claim 1 being 1-ethyl-3-carboxy-4-oxo-1, 4 dihydro-1,8-naphthyridine-7-carboxaldehyde-thio carbohydrazone.

12. Compound according to claim 1 being 1-[7(1-ethyl-3-carboxy-4-oxo-1,4 dihydro-1,8-naphthyrilidene amino)]2 mercapto-1,3,5-triazole.

13. Compound according to claim 1 being N-[7(1-ethyl-3-carboxy-4-oxo-1,4 dihydro-1,8-naphthyrilidene)]-$N^1$-[2(5-nitrofurylidene)]-azine.

14. Compound according to claim 1 being 1-ethyl-3-carboxy-4-oxo-1, 8 naphthyridine-7-carboxaldoxime.

15. Compound according to claim 1 being 1-ethyl-3-carboxy-4-oxo-1,4-dihydro-1,8-naphthyridine-7-carboxaldehyde semicarbazone.

16. Compound according to claim 1 being 1-[7-(1-ethyl-3-carboxy-4-oxo-1,4 dihydro-1,8-naphthyrilidene amino)]guanidine.

17. Compound according to claim 1 being 1-ethyl-3-carboxy-4-oxo-1, 4-dihydro-1,8-naphthyrilidene-7-carboxaldehyde carbohydrazone.

18. Compound according to claim 1 being 1-[7-(1-ethyl-3-carboxy-4-oxo-1,4-dihydro-1,8-naphthyrilidene amino)]oxazolidone.

19. Compound according to claim 1 being 1-ethyl-3-carboxy-4-oxo-1, 4-dihydro-1,8-naphthyridine-7-carboxaldehyde-($\beta$-hydroxyethyl) nitrone.

20. Compound according to claim 1 being 1-ethyl-3-carboxy-4-oxo-1,4-dihydro-1,8-naphthyride-7-carboxaldehyde(N-ethyl)hydrazine.

21. Compound according to claim 1 being 1-ethyl-3-carboxy-4-oxo-1,4-dihydro-1,8-naphthyridine-7-(phenyl-amino)carboxaldehyde; m.p. 290°.

22. Compound according to claim 1 being 1-ethyl-3-carboxy-4-oxo-1, 4-dihydro-1,8 naphthyridine-7-[(4-ethoxy-phenylamino)]carboxaldehyde.

23. Compound according to claim 1 being 1-ethyl-3-carboxy-4-oxo-1,4-dihydro-1,8-naphthyridine-7-carboxaldoxime.

24. A pharmaceutical composition comprising an antibacterial effect amount of the compound claim 1 and a pharmaceutically acceptable carrier.

25. A feed premix including an effective amount of the compound of claim 1.

26. An animal feed comprising an animal foodstuff and an effective amount of the compound of claim 1.

* * * * *